United States Patent
Roitman

(10) Patent No.: US 7,226,752 B1
(45) Date of Patent: Jun. 5, 2007

(54) METHODS FOR DETECTING AN ANALYTE IN A SAMPLE

(75) Inventor: Daniel B. Roitman, Menlo Park, CA (US)

(73) Assignee: Avago Technologies General IP (Singapore) Pte. Ltd., Singapore (SG)

(*) Notice: Subject to any disclaimer, the term of this patent is extended or adjusted under 35 U.S.C. 154(b) by 0 days.

(21) Appl. No.: 11/336,569

(22) Filed: Jan. 19, 2006

(51) Int. Cl.
*G01N 33/00* (2006.01)
(52) U.S. Cl. ............. 435/7.92; 435/7.1; 435/7.93; 435/7.94; 436/518; 436/164; 436/172
(58) Field of Classification Search ............. 435/6, 435/7.1, 7.9, 7.91–7.95; 436/501, 518, 524, 436/164, 172, 536–538
See application file for complete search history.

(56) References Cited

U.S. PATENT DOCUMENTS

| | | | |
|---|---|---|---|
| 5,807,675 A * | 9/1998 | Davalian et al. ............. 435/6 |
| 6,274,323 B1 | 8/2001 | Bruchez et al. |
| 6,326,144 B1 * | 12/2001 | Bawendi et al. ............. 435/6 |
| 6,432,662 B1 | 8/2002 | Davis et al. |
| 6,500,622 B2 | 12/2002 | Bruchez, Jr. et al. |
| 6,630,307 B2 | 10/2003 | Bruchez et al. |
| 6,649,138 B2 | 11/2003 | Adams et al. |
| 6,653,080 B2 | 11/2003 | Bruchez et al. |
| 6,682,596 B2 | 1/2004 | Zehnder et al. |
| 6,734,420 B2 | 5/2004 | Empedocles et al. |
| 6,759,235 B2 | 7/2004 | Empedocles et al. |
| 6,815,064 B2 | 11/2004 | Treadway et al. |
| 6,838,243 B2 | 1/2005 | Lai et al. |
| 6,858,711 B2 | 2/2005 | McGall et al. |
| 2002/0155507 A1 * | 10/2002 | Bruchez et al. ............. 435/7.2 |
| 2003/0099968 A1 * | 5/2003 | Weiss et al. ............. 435/6 |
| 2003/0175785 A1 * | 9/2003 | Patel et al. ............. 435/6 |

* cited by examiner

*Primary Examiner*—Long V. Le
*Assistant Examiner*—Gary W. Counts

(57) ABSTRACT

Methods for detecting the presence of an analyte in a sample are provided. Aspects of the methods include mixing a sample with an indirectly-detectable labeled binding member that includes a label moiety. The mixing produces a first composition. Unbound labeled binding member is then separated from any resultant binding complexes to produce a second composition that includes the binding complexes. A second light emitted by a light wavelength converter that is excited by a first light generated by the labeled binding member of the binding complexes of the second composition is then detected to detect the presence of the analyte in the sample. Embodiments also include kits and systems that find use in practicing the subject methods.

18 Claims, 4 Drawing Sheets

METHODS FOR DETECTING AN ANALYTE IN A SAMPLE

BACKGROUND

Many analytical techniques employed today in a variety of different applications involve determining the presence or absence of a substance, i.e., an analyte, in a sample. Chemiluminescent assays are among the most sensitive assays for analytes in a sample that can be achieved by optoelectronic means. In such assays, an enzyme converts a substrate to a chemiluminescent product in the presence of an analyte of interest, where light emitted by the product is then detected as an indicator of the presence of analyte in the sample being assayed. One well-known and often used chemiluminescent substrate is luminol (3-aminophthalhydrazide or 5-amino-2,3-dihydro-1,4-phthalazinedione). In the presence of a peroxidase and peroxide, luminol is converted to a product that emits light by a chemiluminescent mechanism.

As is known in the art, luminol has a peak emission of around 425 nm. This peak emission wavelength makes luminol-based signal producing systems less attractive for use in conjunction with silicon-based detectors, since silicon-based detectors are not very sensitive in this emission region.

SUMMARY OF THE INVENTION

Methods for detecting the presence of an analyte in a sample are provided. Aspects of the methods include mixing a sample with an indirectly-detectable labeled binding member that includes a label moiety to produce a first composition. Unbound labeled binding member is then separated from any resultant binding complexes to produce a second composition that includes the binding complexes. A second light emitted by a light wavelength converter that is excited by a first light generated by the labeled binding member of the binding complexes of the second composition is then detected to detect the presence of the analyte in the sample. Embodiments also include kits and systems that find use in practicing the subject methods.

DEFINITIONS

Figure 1:
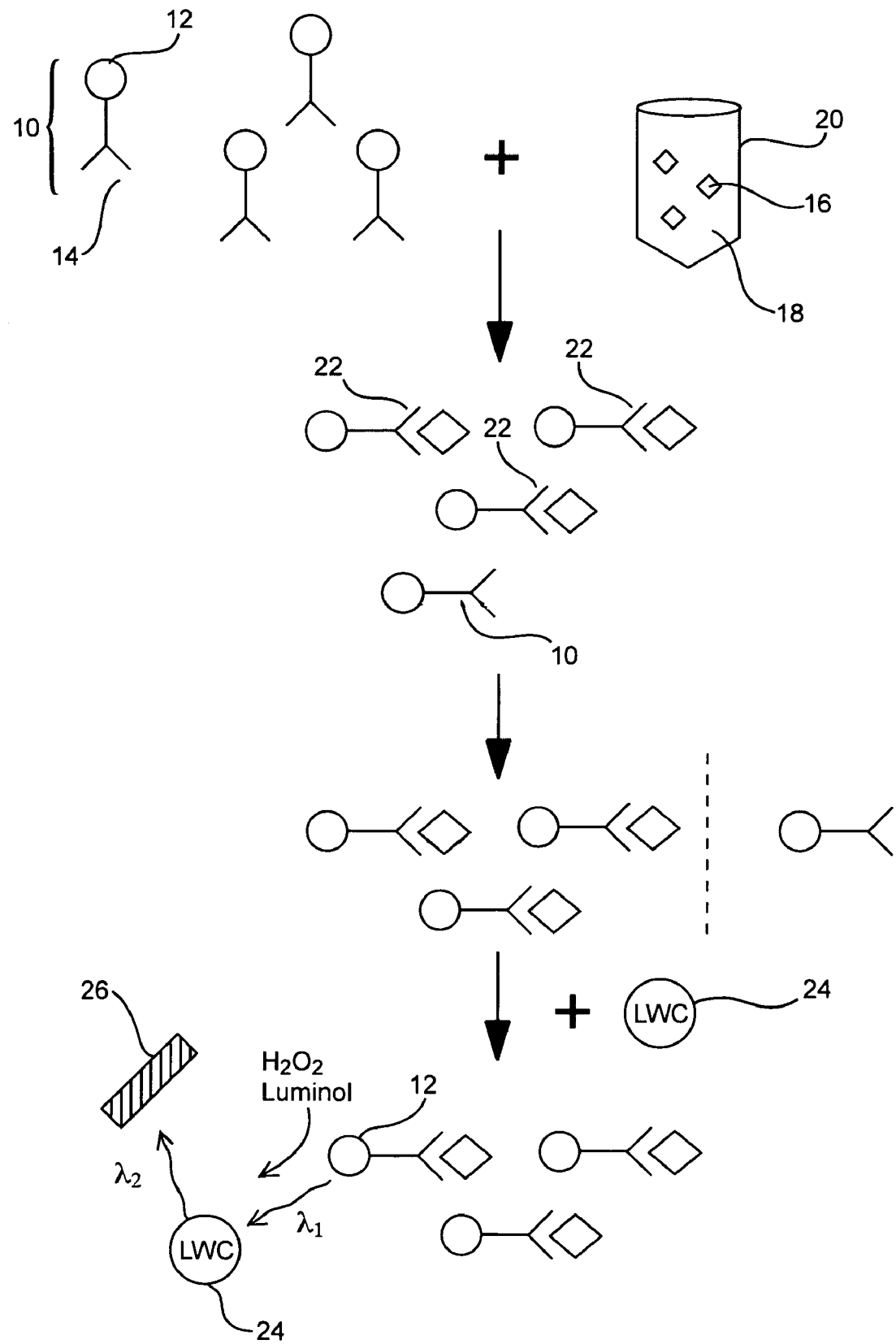
FIG. 1 provides a schematic diagram of a first assay format that is employed in representative embodiments of the invention.

The terms "deoxyribonucleic acid" and "DNA" as used herein mean a polymer composed of deoxyribonucleotides.

The term "oligonucleotide" as used herein denotes single stranded nucleotide multimers of from about 10 to 100 nucleotides and up to 200 nucleotides in length, or longer, e.g., up to about 500 nucleotides or longer. Oligonucleotides are usually synthetic and, in certain embodiments, are under 100, e.g., under 50 nucleotides in length.

A "moiety" is a part of a molecule having a characteristic chemical, biochemical, structural and/or pharmacological property or function. As used herein, the term moiety refers to a subpart of a molecule (for instance, a protein) that retains an independent biochemical or structural activity from the remainder of the molecule, for instance the ability to generate a detectable signal such as luminescence or fluorescence, or to bind or associate or interact with a target. A single molecule may have multiple moieties, each having an independent function.

As used herein, "enzyme" refers to a moiety, e.g., protein or functional domain thereof, specialized to catalyze or promote a specific chemical reaction, e.g., conversion of substrate to a chemiluminescent product.

As used herein, the term "substrate" refers to a compound that is changed in a reaction catalyzed by an enzyme into a second compound. Substrates include chemiluminescent substrates such as luminol that are converted in an enzyme catalyzed reaction from a first non-luminescent product to a second, luminescent product.

The terms "reference" refers to a known value or set of known values against which an observed value may be compared, i.e., to a "control."

As used herein, "known" means that the value represents an understood parameter.

The phrase "first light" refers to light having a spectral maximum at a first wavelength.

The phrase "second light" refers to light having a spectral maximum at a second wavelength.

DETAILED DESCRIPTION

Methods for detecting the presence of an analyte in a sample are provided. Aspects of the methods include mixing a sample with an indirectly-detectable labeled binding member that includes a label moiety. The mixing produces a first composition. Unbound labeled binding member is then separated from any resultant binding complexes to produce a second composition that includes the binding complexes. A second light emitted by a light wavelength converter that is excited by a first light generated by the labeled binding member of the binding complexes of the second composition is then detected to detect the presence of the analyte in the sample. Embodiments also include kits and systems that find use in practicing the subject methods.

Before the present invention is described in greater detail, it is to be understood that this invention is not limited to particular embodiments described herein. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood in the art to which this invention belongs.

Although any methods and materials similar or equivalent to those described herein can also be used in the practice or testing of the present invention, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It must be noted that as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

Each of the individual embodiments described and illustrated herein has discrete components and features which may be readily separated from or combined with the features of any of the other several embodiments without departing from the scope of the present invention. Any recited method can be carried out in the order of events recited or in any other order which is logically possible.

In further describing the subject invention, embodiments will be described first in greater detail, followed by a review of different applications in which the aspects of the invention find use. In addition, kits and systems that find use in certain embodiments will be described in greater detail.

Methods

As summarized above, the subject invention provides methods and compositions for detecting the presence of an analyte in a sample, where the detection may be qualitative or quantitative. Embodiments of the methods include producing a first composition by mixing the sample to be assayed and an indirectly-detectable labeled binding member that includes a label moiety. The mixing produces a first composition. The first composition includes binding complexes of the labeled first binding member and a second binding member, where the identity of the second binding member may vary depending on the particular assay format employed (e.g., sandwich or competitive), as reviewed in greater detail below. The resultant binding complexes are then separated from any unbound labeled binding member to produce a second composition. Binding complexes present in the second composition are then detected to detect the presence of analyte in the sample.

To detect the binding complexes of the second composition, aspects of the invention include the use of label moieties in the labeled binding members that indirectly produce what will be referred to herein as first light, i.e., light having a spectral maximum at a first wavelength. As reviewed in greater detail below, the first light is produced in certain embodiments from a product of a reaction catalyzed by the label moiety of the labeled binding member. For example, where the label moiety is an enzyme, the first light is produced by a product of a substrate conversion reaction catalyzed by the enzyme, as reviewed in greater detail below. As such, the labeled binding members of the second composition are not directly detectable, but instead indirectly produce first light.

Embodiments of the invention include the use of a light wavelength converter that serves to convert first light to second light having a spectral maximum at a second wavelength. In certain embodiments, the light wavelength converter converts the wavelength of light by absorbing first light and emitting second light. By including the light wavelength converter in the second composition, the binding complexes in the second composition are then detected by detecting the second light emitted by the light wavelength converter in response to excitation by the first light generated indirectly by the label moiety of the labeled binding member. Aspects of the invention include using a detector having a greater sensitivity at the second wavelength as compared to the first wavelength.

Light Wavelength Converter

Any convenient light wavelength converter that generates second light having a spectral emission maximum at a desired second wavelength in response to excitation by first light, e.g., generated by an enzyme catalyzed conversion of a luminescent product, may be employed. In certain embodiments, the light wavelength converter is one that participates in an "energy transfer" relationship with the first light producing component, e.g., product emitting the first light, produced by the label moiety of the labeled binding member. As used herein, "energy transfer" refers to the process by which first light emitted by a first component is absorbed by a second component, where the second component then emits second light in response to absorbing the first light. As used herein, "energy transfer pair" refers to any two components that participate in energy transfer.

The light wavelength converter employed in embodiments of the invention has a large Stokes shift, such that its emission maximum is separated from its absorption maximum by at least 100 nm, such as by at least 150 nm, including at least 200 nm, where the Stokes shift may be at as great as 500 nm or more. The light wavelength converter is chosen at least in part in view of the wavelength of the first light produced by the indirect label, and in certain embodiments has an absorption maximum ranging from about 350 to about 550 nm, such as from about 375 to about 500 nm, including from about 400 to about 450 nm. In certain embodiments, the light wavelength converter has an emission maximum ranging from about 500 to about 1000 nm, such as from about 550 to about 850 nm, including from about 600 to about 800 nm.

In certain embodiments of interest, the light wavelength converter is a luminescent nanoparticle, also known as a semiconductor nanoparticle. Luminescent nanoparticles are inorganic crystallites that, in certain embodiments may have a longest dimension (e.g., width, height, length, diameter etc., depending on the shape of the crystallite) that ranges from about 1 nm to about 1000 nm, such as from about 2 nm to about 50 nm, and including from about 2 nm to about 20 nm. A luminescent nanoparticle is capable of emitting light upon excitation (i.e., the semiconductor nanoparticle is luminescent) and includes a "core" of one or more first semiconductor materials, and may optionally be surrounded by a "shell" of a second semiconductor material. A semiconductor nanoparticle core surrounded by a semiconductor shell is referred to as a "core/shell" semiconductor nanoparticle. The surrounding "shell" material has, in certain embodiments, a bandgap energy that is larger than the bandgap energy of the core material and may be chosen to have an atomic spacing close to that of the "core" material. The core and/or the shell can each be a semiconductor material including, but not limited to, those of group II-VI (ZnS, ZnSe, ZnTe, CdS, CdSe, CdTe, HgS, HgSe, HgTe, MgS, MgSe, MgTe, CaS, CaSe, CaTe, SrS, SrSe, SrTe, BaS, BaSe, BaTe, and the like), group III-V (GaN, GaP, GaAs, GaSb, InN, InP, InAs, InSb, and the like) and group IV (Ge, Si, and the like) materials, and an alloy or a mixture thereof.

A semiconductor nanoparticle is, optionally, surrounded by a "coat" of an organic capping agent. The organic capping agent may be any number of materials, but has an affinity for the semiconductor nanoparticle surface. In general, the capping agent can be an isolated organic molecule, a polymer, an inorganic complex, and an extended crystalline structure. The coat is used to convey solubility, e.g., the ability to disperse a coated semiconductor nanoparticle homogeneously into a chosen solvent, functionality, binding properties, or the like. In addition, the coat can be used to tailor the optical properties of the semiconductor nanoparticle.

In certain embodiments, the semiconductor nanoparticles used as light wavelength converters will have a capability of absorbing radiation over a broad wavelength band (as discussed in Published U.S. Patent Application Publication No. 20040166505). In certain embodiments, semiconductor nanoparticles absorb every wavelength of light shorter in wavelength than the emission wavelength of the nanoparticle. As such, the semiconductor nanoparticles absorb a wavelength at the spectral maximum of the first light. In addition, these semiconductor nanoparticles may have a capability of emitting radiation within a narrow wavelength band having a bandwidth of about 40 nm or less, such as about 20 nm or less, (as discussed in Published U.S. Patent Application Publication No. 20040166505).

The selection of the materials and the physical properties of the semiconductor nanoparticles affects the characteristic spectral emission wavelength of the semiconductor nanoparticles. Thus, a given composition of a semiconductor nanoparticle as listed above will be selected based upon the spectral region in which the detector use to detect the second light has useable sensitivity, e.g., maximum sensitivity. For example, semiconductor nanoparticles that emit energy in the visible range include, but are not limited to, CdS, CdSe, CdTe, ZnSe, ZnTe, GaP, and GaAs. Semiconductor nanoparticles that emit energy in the near IR range include, but are not limited to, InP, InAs, InSb, PbS, and PbSe. As an illustration of selection of the emission wavelength by varying the composition of the material of the semiconductor nanoparticle, when CdS, having an emission wavelength of 400 nm in a nanoparticle of a given structure, is alloyed with CdSe, having an emission wavelength of 530 nm in a nanoparticle structure, the wavelength of the emission from a plurality of identically sized nanoparticles may be set to any wavelength in the wavelength range from 400 nm to 530 nm depending on the ratio of S to Se present in the semiconductor material.

As indicated above, the wavelength of the narrow wavelength band of light emitted by the semiconductor nanoparticle (i.e., second light) further depends on the physical properties, such as size, of the semiconductor nanoparticle. The wavelength band of the second light emitted by the semiconductor nanoparticle is determined by the size of the core and/or the size of the core and the size of the shell, depending on the composition of the core and shell of the semiconductor nanoparticle. For example, large CdSe cores that are over six nanometers in diameter may be used to prepare 655 nm emitting semiconductor nanoparticles, while relatively small CdSe cores with diameters of less than three nanometers may be used to prepare the 525 nm emitting semiconductor nanoparticles. In another example, a nanoparticle composed of a 3 nm core of CdSe and a 2 nm thick shell of CdS will emit a second light with a spectral maximum at 600 nm. In contrast, a nanoparticle composed of a 3 nm core of CdSe and a 2 nm thick shell of ZnS will emit a second light with a spectral maximum at 560 nm.

As such, many alternatives to changing the size of the semiconductor nanoparticles to set the emission wavelength of semiconductor nanoparticles exist. These alternatives include: (1) varying the composition of the nanoparticle, and (2) adding one or more concentric shells around the core of the particle. It should be noted that different wavelengths can also be obtained in multiple shell-type semiconductor nanoparticles by using different semiconductor materials in different shells, i.e., by not using the same semiconductor material in each of the concentric shells.

Luminescent nanoparticles that find use as light wavelength converters in the subject methods include, but are not limited to those known in the art as quantum dots, which are further described in U.S. Pat. Nos. 6,838,243; 6,815,064; 6,759,235; 6,734,420; 6,682,596; 6,653,080; 6,649,138; 6,630,307; 6,500,622; and 6,274,323.

Figure 4A:
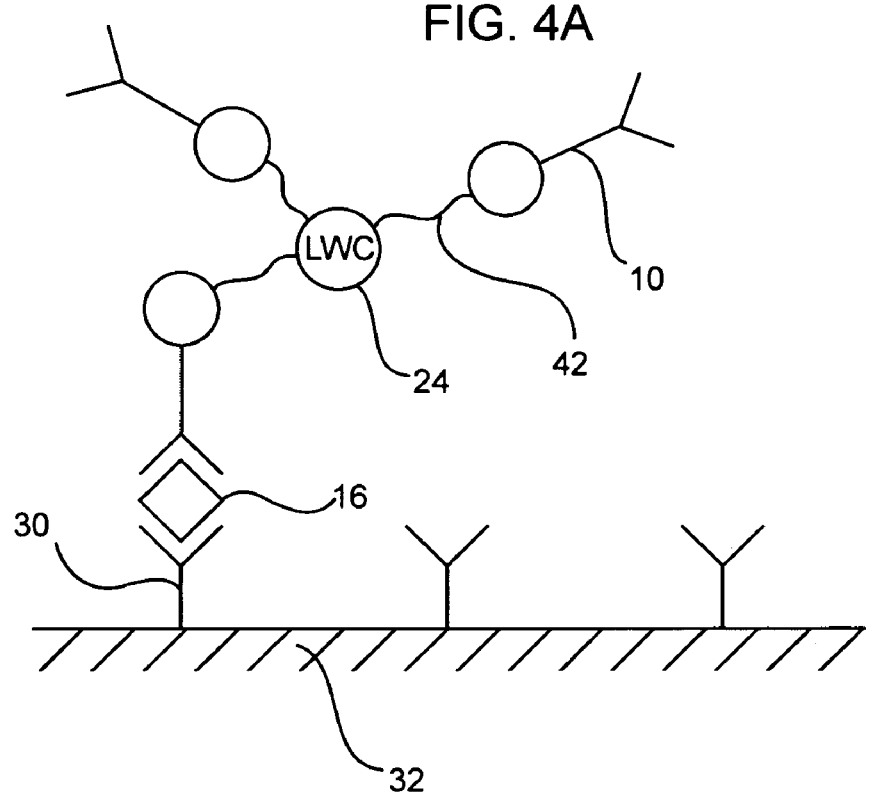
FIGS. 4A and 4B provide views of alternative light wavelength converter formats employed in different embodiments of the invention.

As mentioned above, the light wavelength converter is provided in the second composition. In certain embodiments, the light wavelength converter is stably associated with the labeled binding member. In certain of these embodiments, the light wavelength converter is linked, e.g., conjugated, to the labeled binding member, e.g., as shown in FIG. 4A described in greater detail below. The light wavelength converter may be directly linked to the labeled binding member or may be linked via a linker moiety, such as via a chemical linker, so that the light wavelength converter and labeled binding member are physically linked together, e.g., by covalent chemical bonds, by physical forces such van der Waals or hydrophobic interactions, by a specific binding pair interaction (e.g., avidin/biotin, antibody/antigen, etc.), encapsulation, embedding, or the like. Where the light wavelength converter is a luminescent nanoparticle, e.g., as reviewed above, labeled binding member(s) may be linked to the surface thereof. In a variation of this embodiment, the light wavelength converter is present on a solid support surface employed in the assay. For example, in those embodiments where the binding complex to be detected is immobilized on a surface of a solid support, the light wavelength converter may also be immobilized on the surface of the solid support.

Figure 4B:
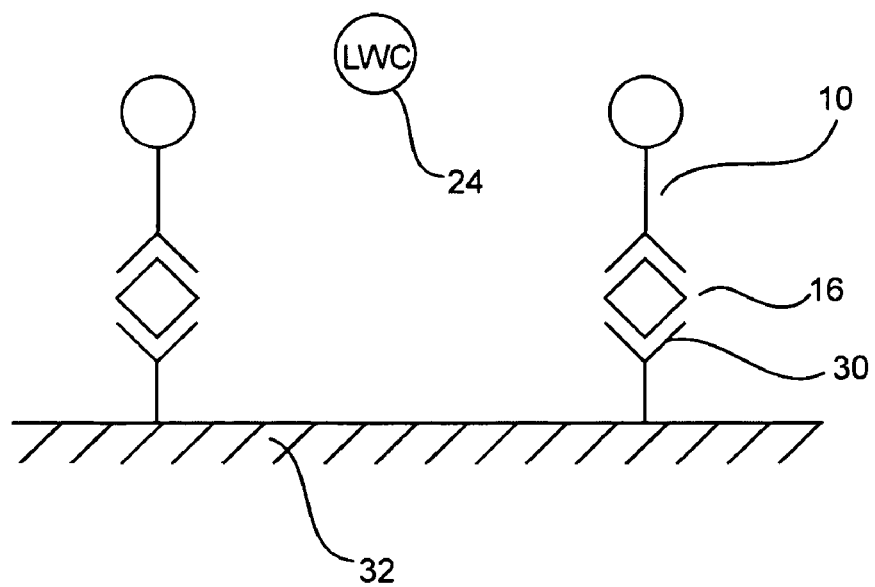

In yet other embodiments, the light wavelength converter is not stably associated with the labeled binding member, but is instead free in a fluid composition in which the labeled binding member is present, as shown in FIG. 4B described in greater detail below. By "free" is meant that the light wavelength converter is not immobilized or otherwise stably associated with another entity in the composition, but is free to move about the fluid composition. In representative embodiments where the complexes that include the labeled binding member are immobilized on the surface of a solid support, the second composition that includes the light wavelength converter is a fluid composition that contacts the surface of the solid support displaying the complexes.

Second Light Detection

The second light from the light wavelength converter may be detected using any convenient detector that generates an electrical signal in response to detection of the second light. Detectors of interest include, but are not limited to: photomultiplier tubes (PMTs), avalanche photodiodes (APDs), charge-coupled devices (CCDs); complementary metal oxide semiconductors (CMOS detectors); silicon PIN photodiodes; and the like. In certain embodiments, the second light generated by the light wavelength converter is detected using a silicon-based detector. The term silicon-based detector means a detector that employs a silicon-containing material in the detector element of the detector, where representative such detectors include, but are not limited to: APDs, CCDs; CMOS detectors; silicon PIN photodiodes; and the like. In certain embodiments, the detector is a detector that has its greatest efficiency of detection, and is therefore most sensitive, in the wavelength range of about 600 to 1000 nm, such as from about 650 to 950 nm. In certain of these embodiments, the silicon-based detector is a silicon PIN photodiode.

Where desired, signal detection may be enhanced by using a light collection device. Any convenient light collection device may be employed that enhances the collection of photons of the second light, where light collection devices of interest include, but are not limited to: lenses, mirrors, diffractive elements, optical waveguides, etc., which act to efficiently collect the second light emitted by the second composition and channel it to the detector.

Processing of Detected Signal

The second light emitted by the light wavelength converter is related to the presence of the analyte(s) of interest in the fluid sample that has been assayed. The second light can be detected to determine qualitatively whether or not the analyte(s) of interest is present in the sample that has been assayed. Alternatively, the second light can be detected determine quantitatively the amount of the analyte(s) of interest in the assayed sample. Quantitative determination is generally made by comparing a parameter of the second light, e.g., intensity, with a reference value (such as the intensity of light generated from a known amount of label). Where a quantitative determination is made, the amount of the binding complexes that are present in the second composition and hence the level of the electric signal produced by the detector is, in certain embodiments, proportional to the amount of analyte in the assayed sample. Depending on the particular assay format, e.g., sandwich or competitive, as reviewed in greater detail below, the amount of binding complexes present in the second composition and hence the level of the electrical signal may be directly or inversely proportional to the amount of analyte in the sample. The above processes can be used to detect the presence of one or more analytes in a sample, either quantitatively or qualitatively, as reviewed in greater detail below.

Assay Formats

As indicated above, embodiments of the methods may employ a number of different formats, including both sandwich and competitive formats. Formats employed in certain embodiments of the invention, including sandwich and competitive formats, are now reviewed in greater detail both generally and in terms of specific embodiments illustrated by figures.

Regardless of the particular assay format that is employed, a first composition is prepared by mixing a sample to be assayed with an indirectly-detectable labeled binding member. The sample that is assayed may be any of a variety of different samples, depending on the particular application in which the subject methods are being performed, where representative samples of interest include, but are not limited to: environmental samples, physiological samples, research samples, etc.

Figure 2:
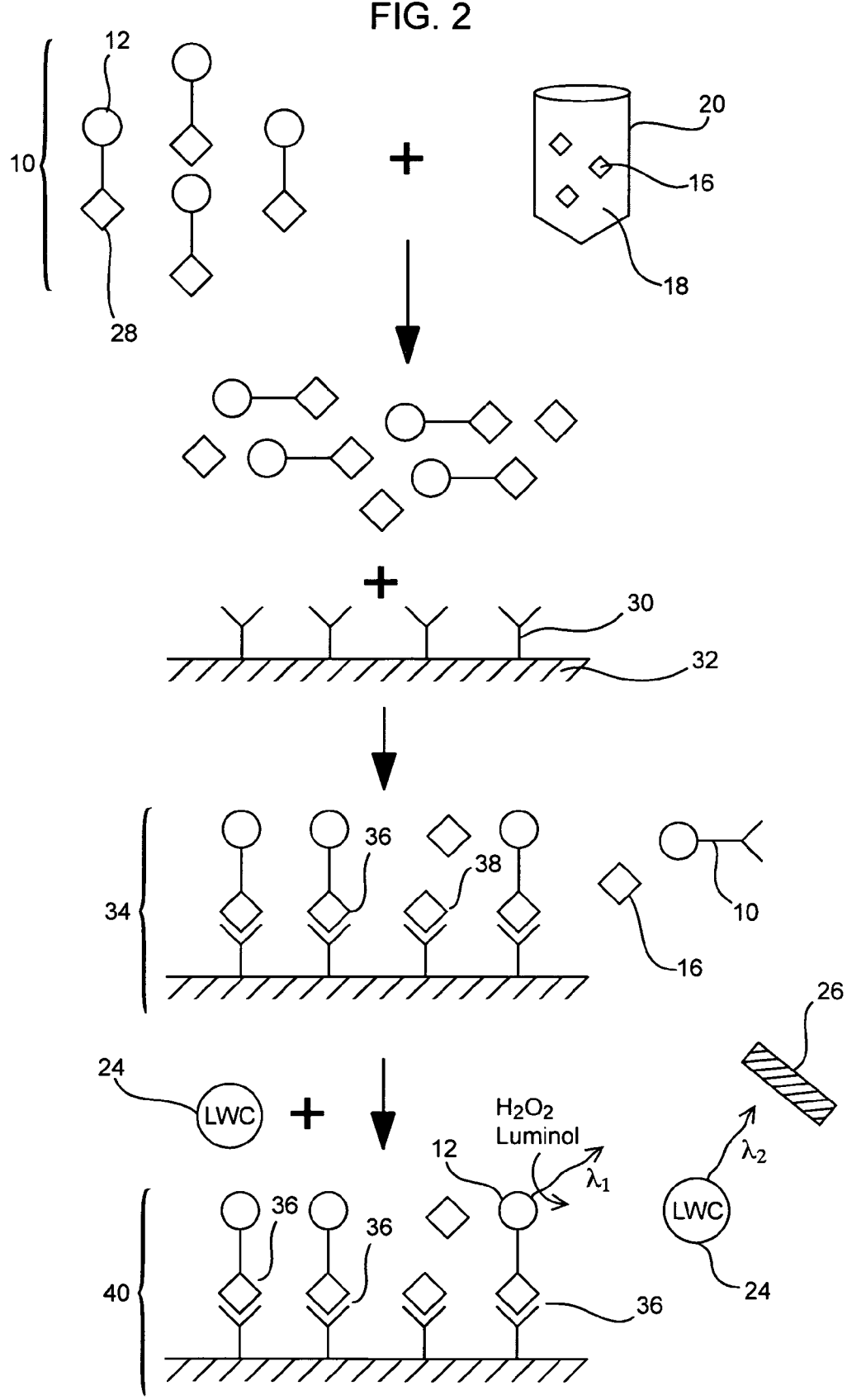
FIG. 2 provides a schematic diagram of a second assay format that is employed in representative embodiments of the invention.
Figure 3:
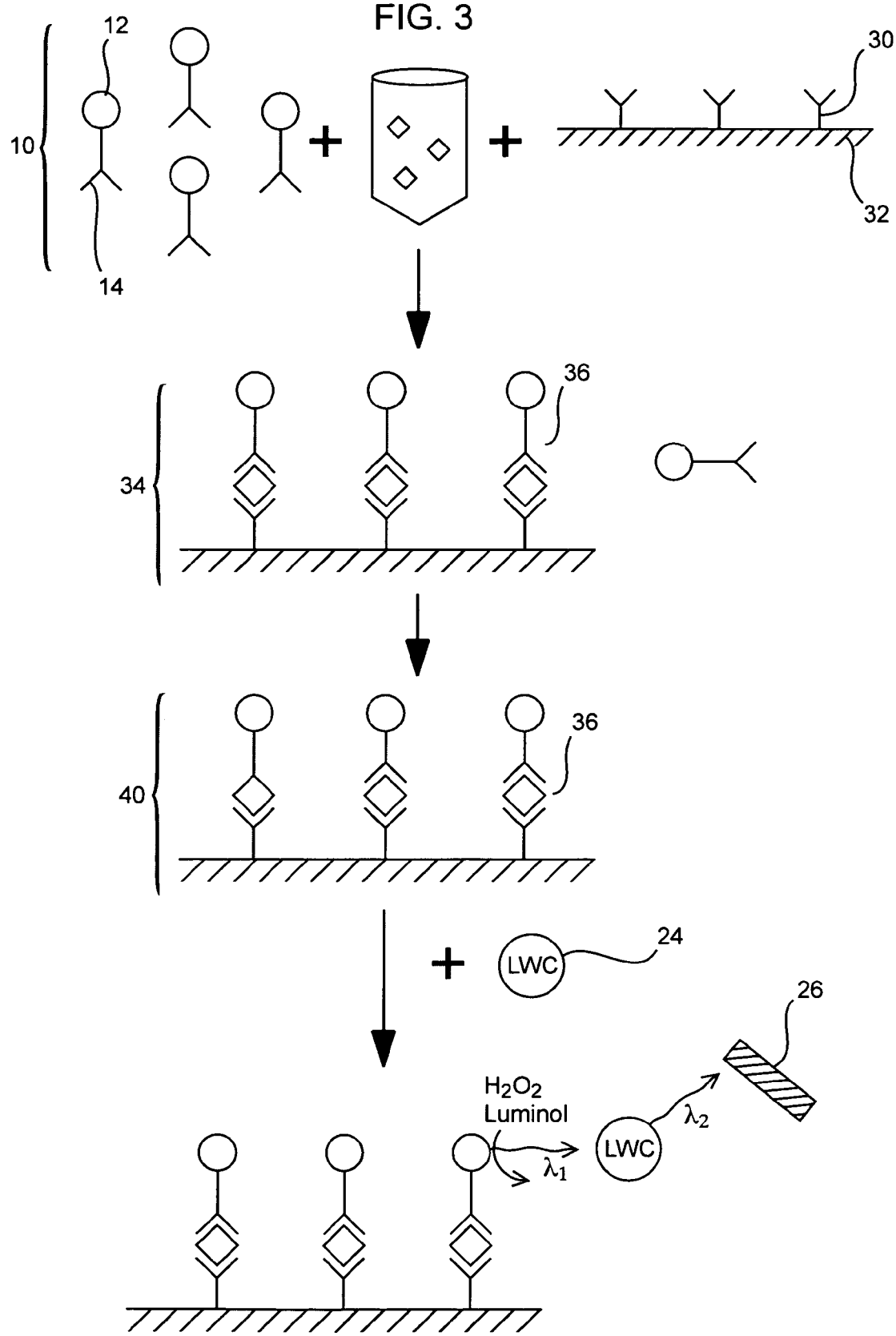
FIG. 3 provides a schematic diagram of a third assay format that is employed in representative embodiments of the invention.

In further describing the invention, three specific embodiments are now reviewed in greater detail in view of FIGS. 1 to 3. FIG. 1 provides a schematic view of a first embodiment of the subject methods that does not employ a second binding member. In FIG. 1, labeled binding members 10 include a horseradish peroxidase (HRP) label 12 conjugated to an antibody moiety 14 that specifically binds to analyte 16 present in sample 18 held in vial 20. The sample 20 and labeled binding members 10 are mixed to produce a first composition, where binding member/analyte complexes 22 are produced in an amount proportional to the amount of analyte in the sample. Also present in the first composition is unbound labeled binding member 10. Next, unbound labeled binding member 10 is separated from the complexes 22, as indicated by the dashed line, to produce a second composition that includes the complexes 22.

Next, a light wavelength converter (e.g., a luminescent nanoparticle) is added to the second composition, along with $H_2O_2$ and luminol. The HRP label in the presence of $H_2O_2$ catalyzes the conversion of the luminol to a chemiluminescent product that generates a first light having a spectral maximum $\lambda_1$ at 425 nm. Light wavelength converter 24 absorbs the first light from the chemiluminescent substrate and, in response, emits second light having a spectral maximum $\lambda_2$ at 655 nm. The second light emitted by light wavelength converter 24 is then detected by silicon-based detector 26 and the electrical signal resulting from the detector employed as a measure of the amount of analyte in the sample. Detector 26 has a greater sensitivity at $\lambda_2$ than at $\lambda_1$.

FIG. 2 provides a schematic view of a second embodiment of the subject methods, which may be characterized as a competitive assay format. In FIG. 2, labeled binding members 10 include a horseradish peroxidase (HRP) label 12 conjugated to a binding member moiety 28 that is a mimetic of the analyte 16 of interest. Binding member moiety 28 may the same as analyte 16, or a binding mimetic thereof that competes with the analyte for binding to a second binding member 30. As in the embodiment shown in FIG. 1, the binding member 10 is mixed with sample 18. In addition, the labeled binding members 10 and sample 18 are mixed with a second binding member 30 immobilized on a surface of a solid support 32. Addition of the sample 18, labeled binding members 10 and support bound second binding member 30 produces a first composition 34, where the first composition 34 includes immobilized binding member complexes 36 that are made up of labeled binding member and second binding member. Also present is binding complex 38 which is made up of analyte 16 and second binding member, as well as free labeled binding member 10 and free analyte 16. Because the labeled binding member and analyte compete for binding to the surface-bound second binding member, the amount of complexes 36 that include a labeled binding member that is present in the first composition is inversely proportional to the amount of analyte in the sample.

Next, unbound labeled binding members 10 are separated, e.g., via washing, from the complexes 36. This step produces a second composition 40 that includes the complexes 36.

Next, a light wavelength converter 24 (e.g., luminescent nanoparticle) is added to the second composition, along with $H_2O_2$ and luminol. The HRP label in the presence of $H_2O_2$ catalyzes the conversion of the luminol to a chemiluminescent product that generates a first light having a spectral maximum at 425 nm. Light wavelength converter 24 absorbs the first light emitted by the luminol and, in response thereto, emits second light having a spectral maximum $\lambda_2$ at 655 nm. The second light emitted by the light wavelength converter is then detected by silicon-based detector 26 (having a greater sensitivity at $\lambda_2$ than at $\lambda_1$) and the electrical signal resulting from the detection employed as a measure of the amount of analyte in the sample.

FIG. 3 provides a schematic view of a third representative embodiment of the subject methods, which may be characterized as a sandwich assay format. In FIG. 3, labeled binding members 10 include a horseradish peroxidase (HRP) label 12 conjugated to an antibody moiety 14 that specifically binds to analyte 16 present in sample 18 held in vial 20. As in the embodiment shown in FIG. 1, the binding member 10 is mixed with sample 18. In addition, the labeled binding members 10 and sample 18 are added to a second binding member 30 immobilized on a surface of a solid support 32. Addition of the sample 18, labeled binding members 10 and support-bound second binding member 30 produces a first composition 34, where the first composition 34 includes immobilized binding member/analyte complexes 36. The complexes are made up of labeled binding member, analyte and second binding member all bound to each other in a sandwich format and immobilized on the surface of support 32. Also present is unbound labeled binding member 10. Next, unbound labeled binding member 10 is separated from the complexes 36, e.g., via washing. Separation produces a second composition 40 that includes the complexes 36.

Next, a light wavelength converter 24, e.g., luminescent nanoparticle, is added to the second composition, along with $H_2O_2$ and luminol. The HRP label in the presence of $H_2O_2$ catalyzes the conversion of the luminol to a chemiluminescent product that generates a first light having a spectral maximum $\lambda_1$, at 425 nm. Light wavelength converter 24 absorbs the first light emitted by the chemiluminescent substrate and, in response, emits second light having a spectral maximum $\lambda_2$ at 655 nm. The second light emitted by the light wavelength converter is then detected by silicon-based detector 26 (having a greater sensitivity at $\lambda_2$ than at $\lambda_1$) and the resultant electrical signal employed as a measure of the amount of analyte in the sample.

FIGS. 4A and 4B illustrate different embodiments of how a light wavelength converter can be located relative to the labeled binding member. FIG. 4A depicts an embodiment where the light wavelength converter is stably associated with the labeled binding member. As shown in FIG. 4A, the light wavelength converter 24 is linked to multiple labeled binding members 10, where each labeled binding member 10 is linked to the light wavelength converter by a linker 42. Light wavelength converter/labeled binding member entity is shown participating in a sandwich assay, where the entity is bound to analyte 16 which, in turn is bound to second binding member 30 that is immobilized on the surface of solid support 32. In a variation of this embodiment, the light wavelength converter may be immobilized on the surface of a solid support 32.

In yet other embodiments, the light wavelength converter is not stably associated with the labeled binding member, but is instead free in a fluid composition in which the labeled binding member is present, e.g., the second composition discussed above, as illustrated in FIG. 4B. By "free" is meant that the light wavelength converter is not immobilized or otherwise stably associated with another entity in the composition, but is free to move about the fluid composition. In certain embodiments where the complexes that include the labeled binding member are immobilized on the surface of a support, the second composition that includes the light wavelength converter is a fluid composition that contacts the surface of the solid support displaying the complexes.

In certain embodiments, multiple analytes in a given sample are detected, where such embodiments are referred to as multiplex embodiments. Any convenient multiplex format may be implemented. For example, one could employ a solid support having on a surface thereof two or more discrete regions, where each region includes a different immobilized second binding member, such that there is one region for each analyte of interest. The particular assay format employed may vary, such as competitive or sandwich (as reviewed above in terms of the figures). The assay may be carried out as described above using labeled binding member(s) and light wavelength converter(s), where the presence or absence of second light detected at a particular region of the substrate surface provides information about whether a particular analyte for which that region of the surface is specific is present.

Indirectly-Detectable Labeled Binding Member

By "indirectly-detectable labeled binding member" is meant a molecule that includes an indirectly-detectable label moiety and a binding member moiety, where the binding member moiety specifically binds to a second molecule. Depending on the particular assay format, the second molecule may vary.

The indirectly-detectable label moiety of this indirectly-detectable labeled binding member is one that is not directly detectable to the detector employed in the assay, but one that interacts with one or more members of a light-producing system to produce a detectable product. In certain embodiments, the ultimate detectable product is a luminescent product, e.g., as described in greater detail below. In certain embodiments, the indirectly-detectable label moiety is an enzymatic moiety that catalyzes the conversion of a substrate to a luminescent product, such as a chemiluminescent product. Enzymes that may be employed include, but are not limited to: hydrolases, such as phosphatases, esterases and glycosidases, oxidoreductases, microperoxidases, and peroxidases. Peroxidases that may be used include, but are not limited to: horseradish peroxidases, where isozymes of horseradish peroxidase that may be used include, but are not limited to: Type VI and Type IX available from Sigma Chemical.

In certain embodiments of interest, the label moiety is an enzymatic label moiety that converts a substrate to a chemiluminescent product. Chemiluminescent products include a compound which becomes electronically excited by a chemical reaction and can then emit light which serves as the first light. A diverse number of families of compounds have been found to provide chemiluminescence under a variety or conditions. One family of compounds is the 2,3-dihydro-1, 4-phthalazinedione family of compounds. Another family of compounds is the 2, 4, 5-triphenylimidazoles, with lophine as the common name for the parent product, where chemiluminescent analogs include para-dimethylamino and -methoxy substituents. Chemiluminescence can also be obtained with oxalates, such as oxalyl active esters, e.g., p-nitrophenyl.

In certain embodiments of interest, the chemiluminescent substrate is chemiluminescent cyclic diacylhydrazide (alternatively referred to in the art as a 2,3-dihydro-1,4-phthalazinedione, comprising the class of luminol, isoluminol, and substituted derivatives of those compounds). The luminol or isoluminol derivatives are those compounds which have the central nucleus of luminol or isoluminol, and have substituent groups on positions which do not destroy the luminescent properties of the underlying nucleus. Substitution that may be present include alkyl (especially lower alkyl of 1–4 carbon atoms), alkoxy (especially lower alkoxy of 1–4 carbon atoms), hydroxy, halogen (especially Cl, I, and Br), carboxyl and carboxylate, acyl, nitro, amino, and the like. These groups may or may not have significant effects upon the luminescence, but are still fundamentally luminol or isoluminol derivatives. Chemiluminescent substrates that may be used include those described in U.S. Pat. No. 4,598,044.

The binding member moiety of the indirectly-detectable labeled binding member is a moiety that specifically binds to a second molecule, where the second molecule may be the analyte, a second binding member, etc., depending on the particular format of the assay. The binding member moiety of the indirectly-detectable labeled binding member is a moiety that has a high binding affinity for a second molecule. By high binding affinity is meant a binding affinity of at least about $10^{-4}$ M, such as at least about $10^{-6}$ M or higher, e.g., $10^{-9}$M or higher. The binding member moiety may be any of a variety of different types of molecules, so long as it exhibits the requisite binding affinity for the second molecule.

In certain embodiments, the binding member moiety is a small molecule ligand. By small molecule ligand is meant a ligand ranging in molecular weight from about 50 to about 10,000 daltons, such as from about 50 to about 5,000 daltons and including from about 100 to about 1000 daltons. The small molecule may be any molecule, as well as a binding portion or fragment thereof, that is capable of binding with the requisite affinity to the second molecule. In certain embodiments, the small molecule is a small organic molecule that is capable of binding to the second molecule. The small molecule may include one or more functional groups necessary for structural interaction with the second molecule, e.g., groups necessary for hydrophobic, hydrophilic, electrostatic or even covalent interactions. The small molecule may also include a region that may participate in (or be modified to participate in) a covalent linkage to the label component of the labeled binding member, without substantially adversely affecting the small molecule's ability to bind to the second molecule. Small molecule affinity ligands may include cyclical carbon or heterocyclic structures and/or aromatic or polyaromatic structures substituted with one or more of the above functional groups. Also of interest as small molecules are structures found among biomolecules, including peptides, saccharides, fatty acids, steroids, purines, pyrimidines, derivatives, structural analogs or combinations thereof. Such compounds may be screened to identify those of interest, where a variety of different screening protocols are known in the art. The small molecule may be derived from a naturally-occurring or synthetic compound that may be obtained from a wide variety of sources, including libraries of synthetic or natural compounds. For example, numerous means are available for random and directed synthesis of a wide variety of organic compounds and biomolecules, including the preparation of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known small molecules may be subjected to directed or random chemical modifications, such as acylation, alkylation, esterification, amidification, etc. to produce structural analogs. The small molecule may be obtained from a library of naturally occurring or synthetic molecules, including a library of compounds produced through combinatorial means, i.e., a compound diversity combinatorial library. When obtained from such libraries, the small molecule employed will have demonstrated some desirable affinity for the protein target in a convenient binding affinity assay. Combinatorial libraries, as well as methods for production and screening thereof, are known in the art and are described in U.S. Pat. Nos. 5,741,713; 5,734,018; 5,731,423; 5,721,099; 5,708,153; 5,698,673; 5,688,997; 5,688,696; 5,684,711; 5,641,862; 5,639,603; 5,593,853; 5,574,656; 5,571,698; 5,565,324; 5,549,974; 5,545,568; 5,541,061; 5,525,735; 5,463,564; 5,440,016; 5,438,119; 5,223,409, the disclosures of which are incorporated herein by reference.

In certain embodiments, the binding member moiety may be a large molecule ligand. By large molecule is meant a ligand having a molecular weight greater than or equal to about 10,000 daltons. In certain embodiments, the large molecule ligand is an antibody, or binding fragment or mimetic thereof. Where antibodies are the large molecule ligand, they may be derived from polyclonal compositions, such that a heterogeneous population of antibodies differing by specificity are employed, or monoclonal compositions, in which a homogeneous population of identical antibodies that have the same specificity for the target protein are employed. As such, the large molecule ligand may be either a monoclonal and polyclonal antibody. In yet other embodiments, the large molecule ligand is an antibody binding fragment or mimetic, where these fragments and mimetics have the requisite binding affinity for the target protein. For example, antibody fragments, such as Fv, F(ab)$_2$ and Fab may be prepared by cleavage of the intact protein, e.g., by protease or chemical cleavage. Also of interest are recombinantly-produced antibody fragments, such as single chain antibodies or scFvs, where such recombinantly produced antibody fragments retain the binding characteristics of the above antibodies. Such recombinantly-produced antibody fragments may include at least the VH and VL domains of the subject antibodies, so as to retain the binding characteristics of the subject antibodies. These recombinantly-produced antibody fragments or mimetics may be readily prepared using any convenient methodology, such as the methodology disclosed in U.S. Pat. Nos. 5,851,829 and 5,965,371. The above-described antibodies, fragments and mimetics thereof may be obtained from commercial sources and/or prepared using any convenient technology.

In certain embodiments, the binding member moiety is a nucleic acid. Nucleic acid domains for use in the subject methods are usually in the range of between about 20 up to about 1000 nucleotides in length, where in certain embodiments they may range from about 25 to about 500 nucleotides in length including from about 25 to about 250 nucleotides in length. The nucleic acid binding member moiety may be made up of ribonucleotides and deoxyribonucleotides as well as synthetic nucleotide residues that are capable of participating in Watson-Crick type or analogous base-pair interactions. The sequence of the nucleic acid affinity ligand is chosen or selected with respect to the sequence of the target molecule to which it binds.

Also suitable for use as binding member moieties are polynucleic acid aptimers. Polynucleic acid aptimers may be RNA oligonucleotides which may act to selectively bind proteins, much in the same manner as a receptor or antibody (Conrad et al., Methods Enzymol. (1996), 267 (Combinatorial Chemistry), 336–367).

Any convenient protocol for producing the labeled binding member may be employed, such as conjugating the binding member moiety to an enzyme label.

Additional Components Present in the First Composition

Depending on the particular embodiment being practiced, one or more additional components may also be present in the first composition. In certain representative embodiments, the first composition further includes a second binding member. The second binding member may bind to the same or different molecule than the binding member moiety of the labeled binding member. For example, in certain embodiments, the second binding member may bind to the same molecule as the binding member moiety of the labeled binding member, e.g., the analyte where the assay being practiced is a sandwich format. Alternatively, the second binding member may bind directly to the labeled binding member, e.g., as occurs in an assay having a competitive format, such that the second binding member and the labeled binding member compete for binding to the analyte.

In certain embodiments of interest, the second binding member is immobilized on the surface of a solid support, e.g., where the support assists in separating unbound labeled binding member from complexes produced in the first composition. A variety of different solid supports may be employed for this purpose. Solid supports that may be employed include, but are not limited to: sheets, beads, or other structures, where such supports may be fabricated from a variety of different materials.

In preparing the first composition, the sample, labeled binding member, and any other components, e.g., second binding member, may be mixed using any convenient protocol. As such, all of the components may be mixed simultaneously, or the components may be added to each other sequentially. While the amounts of the various components that may be mixed will vary and may be chosen purely as a matter of convenience, in representative embodiments, e.g., where a sandwich assay format is employed, the amount of second binding member may be in excess. In yet other embodiments, e.g., competitive formats, the amount of the various components will be chosen in view of the particular assay to be performed, e.g., in view of the amount of analyte that could be in the sample to be assayed, where the amount of second binding member to employ in such embodiments may be readily determined empirically.

Following combination of the sample and binding member(s), the product first composition may be incubated for a period of time sufficient for binding complexes of the labeled binding member to be produced. In representative embodiments, the product first composition is incubated for a period of time ranging from about 5 min to about 5 hours, including from about 30 min to about 2 hours, at a temperature ranging from about 10 to about 50° C., including from about 20 to about 37° C.

The resultant first composition is characterized by the presence of binding complexes, where the binding complexes include a labeled binding member bound to a second molecule. The nature of the second molecule in the binding complexes may vary depending on the particular assay format being employed, where the second molecule may be the analyte, the second binding member. A feature of embodiments of the first composition is that the amount of binding complexes present in the first composition is proportional to the amount of analyte that is present in the sample being assayed.

Resultant complexes in the first composition are then detected using a light wavelength converter as described above to determine the amount of analyte in the sample. In certain embodiments, e.g., to reduce noise, the methods include separating unbound labeled binding member from the complexes present in the first composition. Any convenient separation protocol may be employed, such as size separation protocols, including but not limited to chromatographic protocols, electrophoretic protocols, etc. In certain embodiments that employ a solid support immobilized second binding member, complexes that include this second binding member and the labeled binding member may conveniently be separated from unbound labeled binding member by separating the solid support from the fluid of the first composition, e.g., by washing the surface of the solid support. The above steps are merely representative of different protocols that may be employed to separate the complexes of interest from unbound labeled binding member of the first composition. This separation may conveniently be viewed as producing a second composition that differs from the first composition in that unbound labeled binding members have been separated from complexed labeled binding members.

The next step in the subject methods is to detect the presence of the labeled binding member by detecting second light emitted by a light wavelength converter, as reviewed above. This step may vary depending on the nature of the indirectly-detectable label, and may include the addition to the second composition of one of more reagents, e.g., substrates, additional binding members, etc. In certain embodiments of interest where the label moiety of the labeled binding member is an enzymatic label, this step includes adding a substrate to the second composition that is catalyzed by the enzyme to produce a luminescent product, where in certain embodiments, the luminescent product is a chemiluminescent product as described above.

For the substrate, any convenient chemiluminescent composition that is capable of producing chemiluminescent first light in response to reaction of an oxidant, such as hydrogen peroxide, urea peroxide or sodium perborate, in the presence of a peroxidase, may be employed. The chemiluminescent composition can be a single compound or a combination of compounds which produce the desired first light. In certain embodiments, hydrogen peroxide is provided in the second composition, along with the substrate. Useful chemiluminescent compositions include, but are not limited to, tetrabis (dimethylamino)ethylene, luciferin, lucigenin and oxalyl chloride.

Particularly useful compositions for generating chemiluminescent light include a 2,3-dihydro-1,4-phthalazinedione (also referred to herein as a "DPD"). Any free or conjugated 2,3-dihydro-1,4-phthalazinedione that can be converted to an excited state in a chemiluminescent reaction and then returns to a non-excited state with the emission of light is useful in the practice of this invention. Such compounds include those described in U.S. Pat. No. 4,598,044 (Kricka et al) and Chemiluminescence in Organic Chemistry, Gundermann and McCapra, Springer-Verlag, Berlin, 1987, pages 204–207. Such compounds are generally known as "luminol type hydrazides" and include phthalic hydrazides, naphthalene-1,2-dicarboxylic acid hydrazides, anthracene-2,3-dicarboxylic acid hydrazides, phenathrene-1,2-dicarboxylic acid hydrazides, fluorene-1,2-dicarboxylic acid hydrazides, coronene-1,2-dicarboxylic acid hydrazides, etc.

Of interest in certain embodiments is the DPD is defined by the structure

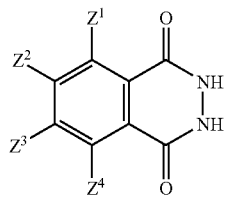

wherein $Z^1$, $Z^2$, $Z^3$ and $Z^4$ are independently hydrogen, alkyl of 1 to 6 carbon atoms (such as methyl, ethyl, isopropyl, t-butyl, sec-pentyl and hexyl), alkenyl of 2 to 6 carbon atoms, such as ethenyl, 1-propenyl, isobutenyl, 2-(N,N-diisopropylamino)vinyl, 2-(N,N-diisobutylamino)vinyl, 2-(N,N-diisopentylamino)vinyl and 2-hexenyl, hydroxy, alkoxy of 1 to 6 carbon atoms (such as methoxy, ethoxy, isopropoxy, t-butoxy and hexoxy), carboxy, amino, including amino substituted with alkyl or alkanoyl, such as methylamino, ethylamino, amido (for example, acetamido and hexanamido), dimethylamino, diethylamino and diisobutylamino, conjugated aminoalkenyl (for example, as defined below) or aminoaryl, including substituted aminoaryl, such as p-(N,N-dimethylamino)phenyl, p-(N,N-diethylamino) phenyl and 5-amino-2,3-dihydro-1,4-phthalazinedion-8-yl (also known as luminyl).

In certain embodiments, at least one of $Z^1$ and $Z^2$ is amino (including substituted amino, as defined above), conjugated aminoalkenyl (including substituted aminoalkenyl as described above) or aminoaryl, such as p-(N,N-dimethylamino)phenyl, p-(N,N-diethylamino)phenyl and 5-amino-2,3-dihydro-1,4-phthalazinedion-8-yl. As used herein, "conjugated aminoalkenyl" refers to a monovalent group capable of electron resonance from the amino group through the alkenyl group to the aromatic ring of the phthalazinedione where it is substituted, and includes for example, a dialkylaminovinyl group, such as 2-(N,N-diisopropylamino)vinyl, 2-(N,N-diisobutylamino)vinyl and 2-(N,N-diisopentylamino)vinyl, and dialkylaminobutadienyl groups, such as 4-(N,N-diethylamino)-1,3-butadien-1-yl.

Alternatively, any adjacent two, adjacent three or all of $Z^1$, $Z^2$, $Z^3$ and $Z^4$ (that is, combinations of two or three adjacent groups, or all four groups) can be taken together to form a fused ring system containing one or more aromatic rings. Such fused rings can be substituted with one or more hydroxy, amino (substituted or unsubstituted as described above) or alkoxy of 1 to 4 carbon atoms (such as methoxy, ethoxy and isopropoxy). In certain embodiments, such fused rings are substituted with one or more primary, secondary or tertiary amines, hydroxy or alkoxy as described above:

Useful DPD compounds include, but are not limited to, luminol, isoluminol, N-(4-aminobutyl)-N-ethylisoluminol hemisuccinimide, N-(6-aminohexyl)-N-ethylisoluminol, N-ethylisoluminol and 7-dimethylaminonaphthalene-1,2-dicarboxylic acid hydrazide. Luminol(5-amino-2,3-dihydro-1, 4-phthalazinedione) and isoluminol(6-amino-2,3-dihydro-1, 4-phthalazinedione) are preferred, and luminol is most preferred.

Other useful classes of DPD compounds are described in the Gundermann and McCapra publication noted above, and include substituted or unsubstituted phthalic acid hydrazides, anthracene-2,3-dicarboxylic acid hydrazides, phenathrene dicarboxylic acid hydrazides, fluorene-1,2-dicarboxylic acid hydrazides, and coronene-1,2-dicarboxylic acid hydrazides, etc., such as the specific structures disclosed in U.S. Pat. No. 5,736,335, the disclosure of which is incorporated herein by reference.

The DPD compounds noted above can be obtained commercially, or be prepared using conventional starting materials and known procedures.

In certain embodiments one or more enhancer compounds may be included in the second composition, which compounds enhance the generation of a chemiluminescent signal. Useful enhancers are described, for example, in U.S. Pat. No. 4,598,044 (Kricka et al), U.S. Pat. No. 4,729,950 (Kricka et al) and U.S. Pat. No. 4,828,983 (McClune), and include such compounds as p-iodophenol, 1,6-dibromonaphth-2-ol, 1-bromonaphth-2-ol, 6-hydroxybenzothiazole, 2,4-dichlorophenol, p-hydroxycinnamic acid, dehydroluciferin, N,N,N'N'-tetramethylbenzidine, p-bromophenol, p-chlorophenol. Other enhancer compounds of interest include those enhancer compounds described in U.S. Pat. Nos. 5,736,335 and 6,432,662.

Utility

The subject methods may be used to screen a sample for the presence or absence of one or more analytes in a sample. The methods may be qualitative or quantitative. Where detection is qualitative, the methods provide a reading of whether or not the analyte is present in the sample being assayed. In yet other embodiments, the methods provide a quantitative detection of whether the analyte is present in the sample being assayed, i.e., an evaluation of the actual amount of the analyte in the sample being assayed. In such embodiments, the quantitative detection may be absolute or, if the method is a method of detecting two or more different analytes in a sample, relative. Therefore, the term "quantifying" when used in the context of quantifying an analyte(s) in a sample can refer to absolute or to relative quantification. Absolute quantification may be accomplished by inclusion of known concentration(s) of one or more control analytes (i.e. standards) and referencing the detected level of the analyte with the known control analyte (e.g., through generation of a standard curve). Alternatively, relative quantification can be accomplished by comparison of detected levels or amounts between two or more different analytes to provide a relative quantification of each of the two or more different analytes, e.g., relative to each other.

The subject methods can be employed to detect the presence of one or more analytes in a variety of different types of samples, including complex samples having large amounts of non-target entities, where the subject methods provide for detection of the analytes(s) with high sensitivity. The sample that is assayed may be from a physiological source. The physiological source may be eukaryotic or prokaryotic, with physiological sources of interest including sources derived from single-celled organisms such as bacteria and yeast and multicellular-organisms, including plants and animals, particularly mammals, where the physiological sources from multicellular organisms may be derived from particular organs or tissues of the multicellular organism, or from isolated cells or subcellular/extracellular fractions derived there from.

Embodiments may be used to detect a wide variety of analytes. Analytes of interest can be proteinacious molecules, such as, but not limited to, proteinacious analytes, including peptides and proteins and fragments thereof, as well as prions and other proteinaceous types of analytes, where the analytes may be a single molecule, a complex that includes two or more molecular subunits, which may or may not be covalently bound to each other, a microorganism, e.g., virus or single celled pathogen, a cell, a multicellular organism or portion thereof, and the like. Analytes of interest may also be nucleic acid analytes, e.g., oligonucleotides, polynucleotides, etc., including RNA, DNA etc.

In addition, embodiments may also be used to screen for compounds that modulate the interaction between the binding domain of the labeled binding member with the binding region of the analyte. The term modulating includes both decreasing (e.g., inhibiting) and increasing (e.g., enhancing) the interaction between the two molecules. A variety of different candidate agents may be screened by the above methods. Candidate agents encompass numerous chemical classes, though typically they are organic molecules, preferably small organic compounds having a molecular weight of more than 50 and less than about 2,500 daltons. Candidate agents comprise functional groups necessary for structural interaction with proteins, particularly hydrogen bonding and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof.

Candidate agents are obtained from a wide variety of sources including libraries of synthetic or natural compounds. For example, numerous methods are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically-produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

Agents identified in the above screening assays find use in a variety of methods, including methods of modulating the activity of the target analyte, and conditions related to the presence and/or activity thereof.

The subject methods may also be readily adapted to high-throughput format, in which multiple samples are assayed simultaneously for a given target analyte or analytes using subject methods. For example, the subject assays may be performed on a multi-well substrate using for example, an automated plate reader device, such as the device described in U.S. Pat. No. 5,670,113, the disclosure of which is herein incorporated by reference. In this manner, multiple fluid samples may be assayed essentially simultaneously, whereby multiple is meant 2 or more.

Kits

Also provided are kits that find use in practicing embodiments of the methods, as described above. For example, in some embodiments, kits for include a labeled binding member, a chemiluminescent substrate and a light wavelength converter, as described above. In addition, the kits may include a second binding member, e.g., immobilized on a surface of a solid support, as well as other components that find use in a given assay, e.g., hydrogen peroxide, buffers, etc. The kit components may be present in separate containers, or one or more of the components may be present in the same container, where the containers may be storage containers and/or containers that are employed during the assay for which the kit is designed. In addition to the above components, the subject kits may further include instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another format would be a computer readable medium, e.g., diskette, CD, etc., on which the information has been recorded. Yet another format that may be present is a website address which may be used via the internet to access the information at a removed site.

Systems

Also provided are systems that find use in practicing the subject methods, as described above. The term system, as used herein, refers to a collection of components that are brought together from two or more disparate sources, e.g., for purposes of practicing the subject methods, where the components that are brought together may or may not have been provided in a "kit" format, as described above. For example, in some embodiments, systems for practicing the subject methods may include at least a labeled binding member, a light wavelength converter and chemiluminescent substrate, where the systems may further include additional components, e.g., hydrogen peroxide, second binding member, etc., as reviewed above.

Although the foregoing invention has been described in some detail by way of illustration and example for purposes of clarity of understanding, certain changes and modifications may be made thereto without departing from the scope of the appended claims.

What is claimed is:

1. A method of detecting the presence of an analyte in a sample, said method comprising:

mixing said sample with a chemiluminescent indirectly-detectable labeled binding member comprising a label moiety to produce a first composition that includes binding complexes comprising said labeled binding member;

separating said unbound labeled binding member from binding complexes present in said first composition to produce a second composition comprising said binding complexes;

adding a light wavelength converter and an oxidant to the second composition;

detecting said binding complexes in said second composition to detect the presence of said analyte in said sample, wherein said detecting comprises detecting second light emitted by said light wavelength converter, said light wavelength converter generating said second light in response to absorbing first light generated by said indirectly-detectable labeled binding member of said binding complexes of said second composition, said first light being generated in response to reaction of said indirectly-detectable labeled binding member with said oxidant.

2. The method according to claim 1, wherein said binding complexes are present in said second composition in amount proportional to the amount of said analyte in said sample.

3. The method according to claim 1, wherein said labeled binding member specifically binds to said analyte.

4. The method according to claim 3, wherein said first composition further comprises a second binding member, and said binding complexes are made up of said labeled binding member, said analyte and said second binding member.

5. The method according to claim 4, wherein said second binding member is immobilized on a surface of a solid support.

6. The method according to claim 1, wherein said labeled binding member does not specifically bind to said analyte.

7. The method according claim 6, wherein said labeled binding member competes with said analyte for binding to a second binding member.

8. The method according to claim 1, wherein said light wavelength converter is at least one of linked directly to said labeled binding member and linked to said labeled binding member via a linker moiety.

9. The method according to claim 8, wherein said light wavelength converter is conjugated to said labeled binding member.

10. The method according to claim 8, wherein said light wavelength converter is immobilized on a surface of a solid support.

11. The method according to claim 1, wherein said light wavelength converter remains unlinked with said labeled binding member in said second composition.

12. The method according to claim 1, wherein said label moiety of said indirectly-detectable labeled binding member is an enzymatic label.

13. The method according to claim 12, wherein said enzymatic label comprises a peroxidase.

14. The method according to claim 12, wherein said enzymatic label converts a substrate into a chemiluminescent product.

15. The method according to claim 14, wherein said substrate is a dihydrophthalazinedione.

16. The method according to claim 15, wherein said substrate is luminol.

17. The method according to claim 1, wherein said light wavelength converter has a Stokes shift of at least about 100 nm.

18. The method according to claim 17, wherein said light wavelength converter comprises a nanoparticle.

* * * * *